(12) United States Patent
Merrill et al.

(10) Patent No.: US 11,008,621 B2
(45) Date of Patent: May 18, 2021

(54) MULTI-COPY REFERENCE ASSAY

(71) Applicant: LIFE TECHNOLOGIES CORPORATION, Carlsbad, CA (US)

(72) Inventors: David Merrill, Millbrae, CA (US); Pius Brzoska, Woodside, CA (US); Zheng Li, San Ramon, CA (US); Wendy Lin, San Francisco, CA (US); Wing Lee, San Leandro, CA (US); Mandi Wong, South San Francisco, CA (US)

(73) Assignee: Life Technologies Corporation, Carlsbad, CA (US)

( * ) Notice: Subject to any disclaimer, the term of this patent is extended or adjusted under 35 U.S.C. 154(b) by 13 days.

(21) Appl. No.: 15/128,076

(22) PCT Filed: Mar. 20, 2015

(86) PCT No.: PCT/US2015/021853
§ 371 (c)(1),
(2) Date: Sep. 21, 2016

(87) PCT Pub. No.: WO2015/143385
PCT Pub. Date: Sep. 24, 2015

(65) Prior Publication Data
US 2017/0096711 A1 Apr. 6, 2017

Related U.S. Application Data

(60) Provisional application No. 61/968,609, filed on Mar. 21, 2014.

(51) Int. Cl.
C12Q 1/68 (2018.01)
C12P 19/34 (2006.01)
C12Q 1/6886 (2018.01)
C12Q 1/6858 (2018.01)
C12Q 1/6851 (2018.01)
C07H 21/04 (2006.01)

(52) U.S. Cl.
CPC ......... *C12Q 1/6886* (2013.01); *C12Q 1/6851* (2013.01); *C12Q 1/6858* (2013.01); *C12Q 2600/156* (2013.01); *C12Q 2600/158* (2013.01); *C12Q 2600/166* (2013.01)

(58) Field of Classification Search
None
See application file for complete search history.

(56) References Cited

U.S. PATENT DOCUMENTS

2006/0134663 A1* 6/2006 Harkin ................ C12Q 1/6837
435/6.11

FOREIGN PATENT DOCUMENTS

| EP | 3119906 B1 | 1/2019 |
| WO | WO-2007/078599 | 7/2007 |
| WO | WO-2015143385 A1 | 9/2015 |

OTHER PUBLICATIONS

You (Expermental and Molecular Pathology, 2012, 92: 281-286).*
Long, S. et al., "Multicopy Reference Assay (MRef)—A Superior Normalizer of Sample Input in DNA Copy Number Analysis", https://www.qiagen.com/nl/resources/download.aspx?id=a0c54902-07a6-493b-9352-885f9063689b&1ang=en, Feb. 2013, 2 Pages.
Mccaughan, F. et al., "Microdissection Molecular Copy-Number Counting (uMCC)—Unlocking Cancer Archives with Digital PCR", *Journal of Pathology*, vol. 216, Jul. 29, 2008, 307-316.
Okuda, K. et al., "Met Gene Copy Number Predicts the Prognosis for Completely Resected Non-Small Cell Lung Cancer", *Cancer Sci*, vol. 99, No. 11, Oct. 23, 2008, 2280-2285.
PCT/US2015/021853, International Search Report and Written Opinion dated Aug. 14, 2015, 20 Pages.
PCT/US2015/021853, Invitation to Pay Additional Fees and Partial Search Report dated Jul. 2, 2015, 9 Pages.
Trinklein, N. D. et al., "Functional Arrays for High Throughput Characterization of Gene Expression Regulatory Elements", Database Accession No. JB130793, Sequence 39820 from Patent EP2021499, Apr. 11, 2013, 1 Page.
Partial European Search Report for Application No. 19151963.6, dated Aug. 1, 2019, 13 pages.

* cited by examiner

*Primary Examiner* — Sarae L Bausch
(74) *Attorney, Agent, or Firm* — Jinhee Chang

(57) ABSTRACT

A method, comprising amplifying a nucleic acid sequence of interest in a sample comprising genomic DNA of a subject; amplifying a reference nucleic acid sequence in the sample; quantifying the amplified sequence of interest relative to the amplified reference sequence; and determining a copy number of the sequence of interest from the relative quantified amplified sequence of interest. The reference sequence may have at least 80% sequence identity to at least one of SEQ ID NO:1-38, such as SEQ ID NO:1-13. Also disclosed are kits and compositions, each comprising a first probe which specifically hybridizes to at least a portion of at least one reference sequence. Also disclosed is a system configured to perform the above method.

6 Claims, 3 Drawing Sheets

Specification includes a Sequence Listing.

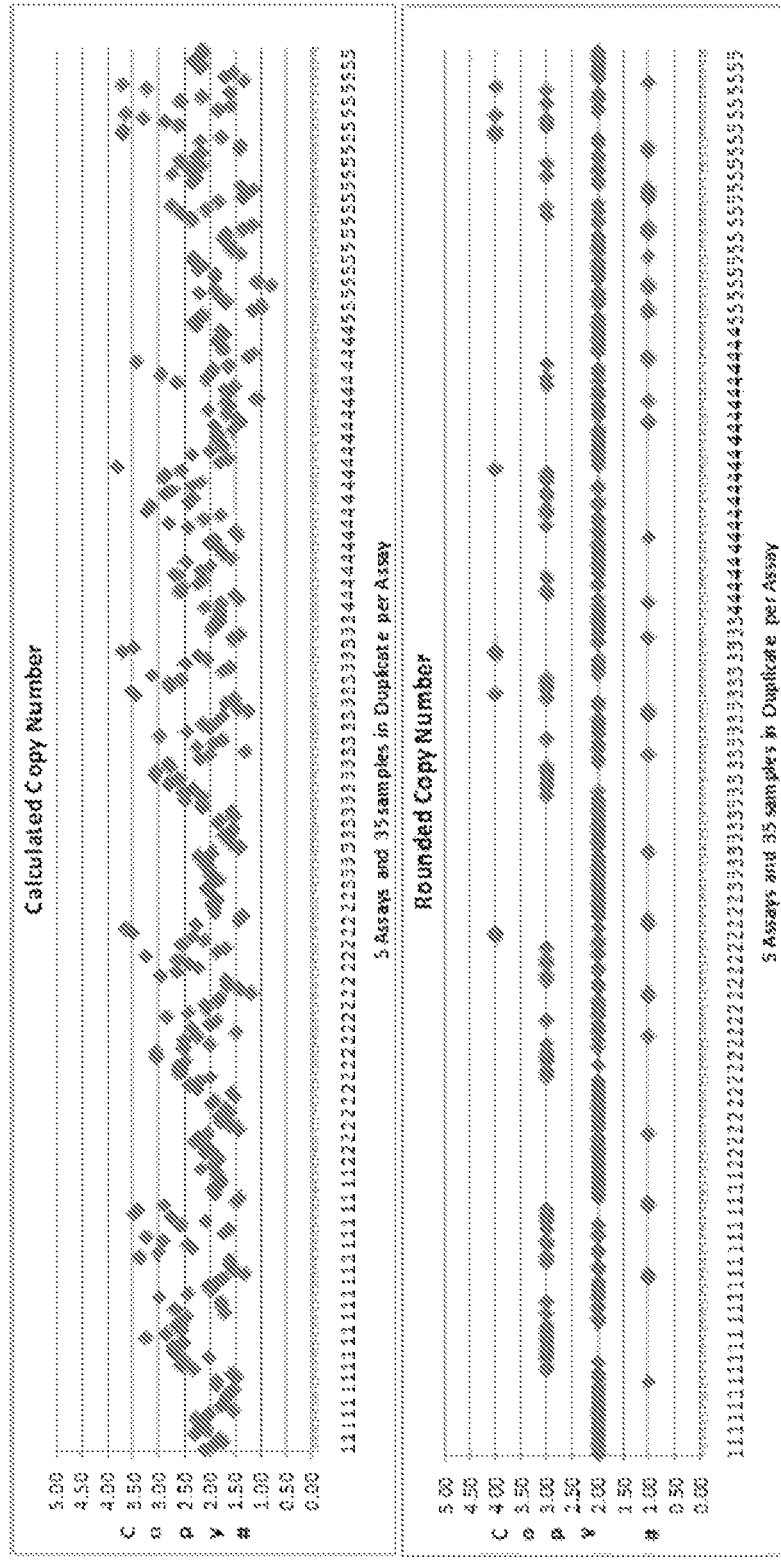

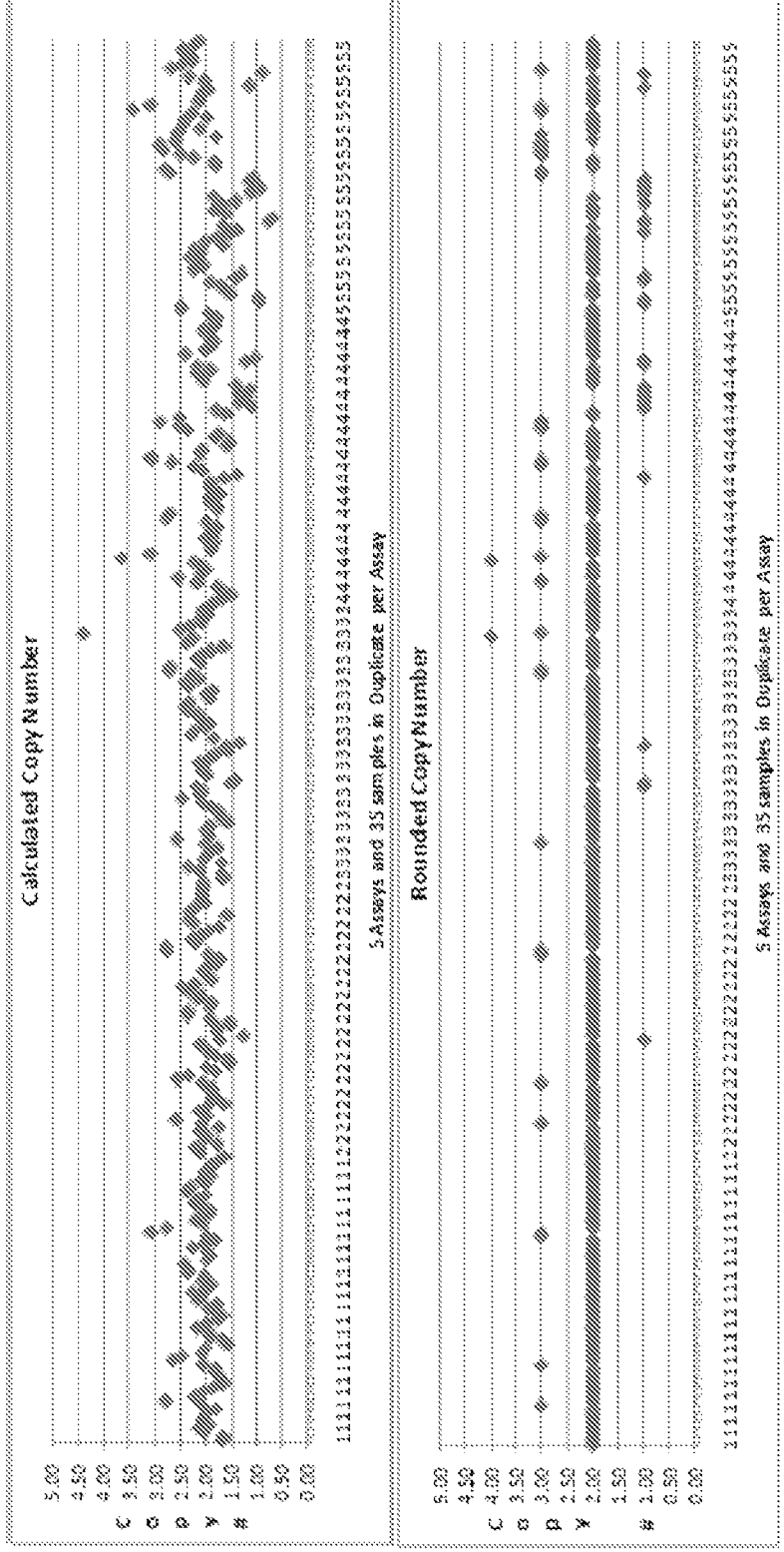

SEQUENCE LISTING

```
<160> NUMBER OF SEQ ID NOS: 31

<210> SEQ ID NO 1
<211> LENGTH: 70
<212> TYPE: DNA
<213> ORGANISM: Homo sapiens
<220> FEATURE:
<221> NAME/KEY: misc_feature
<222> LOCATION: 70
<223> OTHER INFORMATION: n = A,T,C or G

<400> SEQUENCE: 1
ggctgyttgc rgtagtwrts trkswrsmrs mmrmwsrmyg smsrcarrsr arrmarwyws    60
``` twdvwakkmn									70

<210> SEQ ID NO 2
<211> LENGTH: 70
<212> TYPE: DNA
<213> ORGANISM: Homo sapiens

<400> SEQUENCE: 2
ggctgcttgc agtagttgtg tagcagcagc acaatggccg cagacaagga aaacagtttc		60 taggaattcc									70

<210> SEQ ID NO 3
<211> LENGTH: 70
<212> TYPE: DNA
<213> ORGANISM: Homo sapiens

<400> SEQUENCE: 3
ggctgcttgc ggtagttatg tagcagcagc acaatggccg cagacaagga aaacagtttc		60 taggaattcc									70

<210> SEQ ID NO 4
<211> LENGTH: 70
<212> TYPE: DNA
<213> ORGANISM: Homo sapiens

<400> SEQUENCE: 4
ggctgcttgc ggtagttgtc tagcagcagc acaatggccg cagacaagga aaacagtttc		60 taggaattcc									70

<210> SEQ ID NO 5
<211> LENGTH: 70
<212> TYPE: DNA
<213> ORGANISM: Homo sapiens

<400> SEQUENCE: 5
ggctgcttgc ggtagttgtg tagcagcagc acaatggccg cagacaagga aaacagtttc		60 taaaaattcc									70

<210> SEQ ID NO 6
<211> LENGTH: 70
<212> TYPE: DNA
<213> ORGANISM: Homo sapiens

<400> SEQUENCE: 6
ggctgcttgc ggtagttgtg tagcagcagc acaatggccg cagacaagga aaacagtttc		60 taggaattcc									70

<210> SEQ ID NO 7
<211> LENGTH: 70
<212> TYPE: DNA
<213> ORGANISM: Homo Sapiens
<220> FEATURE:
<221> NAME/KEY: misc_feature
<222> LOCATION: 70
<223> OTHER INFORMATION: n = A,T,C or G

<400> SEQUENCE: 7
ggctgcttgc ggtagttgtg tagcagcagc acaatggccg cagacaagga aaacagtttc		60 taggaattcn									70

-continued

```
<210> SEQ ID NO 8
<211> LENGTH: 70
<212> TYPE: DNA
<213> ORGANISM: Homo Sapiens

<400> SEQUENCE: 8
ggctgtttgc ggtagtagtc tgtgtagcag cagcacaatg gccgcagacg aggaaaacag    60
tttctaggaa                                                          70

<210> SEQ ID NO 9
<211> LENGTH: 67
<212> TYPE: DNA
<213> ORGANISM: Homo sapiens

<400> SEQUENCE: 9
agtgcagyrw tgytgactct tccaagctta acatttctca saartcaatt agctttgtac    60
tgggagg                                                             67

<210> SEQ ID NO 10
<211> LENGTH: 67
<212> TYPE: DNA
<213> ORGANISM: Homo sapiens

<400> SEQUENCE: 10
agtgcagcaa tgttgactct tccaagctta acatttctca gaagtcaatt agctttgtac    60
tgggagg                                                             67

<210> SEQ ID NO 11
<211> LENGTH: 67
<212> TYPE: DNA
<213> ORGANISM: Homo sapiens

<400> SEQUENCE: 11
agtgcagcga tgctgactct tccaagctta acatttctca caagtcaatt agctttgtac    60
tgggagg                                                             67

<210> SEQ ID NO 12
<211> LENGTH: 67
<212> TYPE: DNA
<213> ORGANISM: Homo sapiens

<400> SEQUENCE: 12
agtgcagcgt tgctgactct tccaagctta acatttctca caaatcaatt agctttgtac    60
tgggagg                                                             67

<210> SEQ ID NO 13
<211> LENGTH: 67
<212> TYPE: DNA
<213> ORGANISM: Homo sapiens

<400> SEQUENCE: 13
agtgcagtga tgctgactct tccaagctta acatttctca caagtcaatt agctttgtac    60
tgggagg                                                             67

<210> SEQ ID NO 14
<211> LENGTH: 99
<212> TYPE: DNA
<213> ORGANISM: Homo sapiens

<400> SEQUENCE: 14
```

```
gtgtagcagc agcacaatgg ccgcagacaa ggaaaacagt ttctaggaat tcctcgtata    60
taattttata tttttgacaa gattaatgac ccatgctcc                          99

<210> SEQ ID NO 15
<211> LENGTH: 65
<212> TYPE: DNA
<213> ORGANISM: Homo sapiens

<400> SEQUENCE: 15
tgcarmgatg ctgactcttc caagcttaac atttctcaca agtcaattag ctttgtactg    60
ggagg                                                               65

<210> SEQ ID NO 16
<211> LENGTH: 79
<212> TYPE: DNA
<213> ORGANISM: Homo sapiens

<400> SEQUENCE: 16
tgctgactct tccaagctta acatttctca agtcaatt agctttgtac tgggaggagg     60
gcgtgaaggg ctgcttgcg                                                79

<210> SEQ ID NO 17
<211> LENGTH: 148
<212> TYPE: DNA
<213> ORGANISM: Homo sapiens

<400> SEQUENCE: 17
caagggacaa ggaaaaatta tccaaacatt gtttaaaaca atcatcatta attagtaaca    60
cttatccagg ggggttttta acctttcccc cactcaasga ttattctaat gtcagagtag   120
aataaaaaat aagtgcarmg atgctgac                                     148

<210> SEQ ID NO 18
<211> LENGTH: 104
<212> TYPE: DNA
<213> ORGANISM: Homo sapiens

<400> SEQUENCE: 18
ggaggaggaa aataggtagt ttttcaaaag ttttcaaaaa tatgaaaaga agaaatgaaa    60
tggtacttgg aagagattgt tgaaatggga gagactatgg tggc                   104

<210> SEQ ID NO 19
<211> LENGTH: 81
<212> TYPE: DNA
<213> ORGANISM: Homo sapiens

<400> SEQUENCE: 19
caactaaaag gcaatgtcac tccaataatc accagagtaa tcaatttgct tattgctgtc    60
cctttaaata tagttctctg g                                             81

<210> SEQ ID NO 20
<211> LENGTH: 120
<212> TYPE: DNA
<213> ORGANISM: Homo sapiens

<400> SEQUENCE: 20
ggagagacta tggtggcttg tttagaagca gttgagatag atccaattga gatagagata    60
ttgagtatat aaacaaaaga atgacaaatt aatagtgtaa tggataactt gactttggca   120
```

<210> SEQ ID NO 21
<211> LENGTH: 86
<212> TYPE: DNA
<213> ORGANISM: Homo sapiens

<400> SEQUENCE: 21
gtgtaatgga taacttgact ttggcaaata ttgtgaattt ttgtgaaagt acaactaaaa    60
ggcaatgtca ctccaataat caccag                                         86

<210> SEQ ID NO 22
<211> LENGTH: 101
<212> TYPE: DNA
<213> ORGANISM: Homo sapiens

<400> SEQUENCE: 22
gtaatcaatt tgcttattgc tgtcccttta aatatagttc tctggtatca actaacatgt    60
ttttaactaa tgatgcttct taaagaaaag ggaaaagacc t                       101

<210> SEQ ID NO 23
<211> LENGTH: 67
<212> TYPE: DNA
<213> ORGANISM: Homo sapiens

<400> SEQUENCE: 23
ccctgggccc ctcaggggag tccctgctgg acagtgagac agagaatgac catgatgatg    60
ctttcct                                                              67

<210> SEQ ID NO 24
<211> LENGTH: 93
<212> TYPE: DNA
<213> ORGANISM: Homo sapiens

<400> SEQUENCE: 24
gggtttatgt ttgatatrta atgtaatttt ctaatgctaa atcaagtggt aattttgtta    60
gtcaagttga tttagtggct tgggaagaaa gct                                 93

<210> SEQ ID NO 25
<211> LENGTH: 89
<212> TYPE: DNA
<213> ORGANISM: Homo sapiens

<400> SEQUENCE: 25
gagaccccca ggtgttgagg cagggctggg gtgtcccctt ccaaccaggc tgtcaaggcc    60
ccaactctgg ggcagaggca gtggcaggg                                      89

<210> SEQ ID NO 26
<211> LENGTH: 67
<212> TYPE: DNA
<213> ORGANISM: Homo sapiens

<400> SEQUENCE: 26
catccgtttc acctgcagtt gaagatccgt gaggtgccca gaagatcatg cagtcawcag    60
tcccacg                                                              67

<210> SEQ ID NO 27
<211> LENGTH: 83
<212> TYPE: DNA
<213> ORGANISM: Homo sapiens

<400> SEQUENCE: 27

```
gakataagga agctcgagga agagaaaaaa caactggaag gagaaatcat agatttttat    60
aaaatgamag ctgcctctga agc                                           83

<210> SEQ ID NO 28
<211> LENGTH: 145
<212> TYPE: DNA
<213> ORGANISM: Homo sapiens

<400> SEQUENCE: 28
ccgttttgga ggaggaacag attccatgtc cactagaatg gaatgaacaa gaaatggagg    60
aggaaaatag gtagtttttc aaaagttttc aaaaatatga aagaagaaa tgaaatggta    120 cttggaagag attgttgaaa tggga                                          145

<210> SEQ ID NO 29
<211> LENGTH: 102
<212> TYPE: DNA
<213> ORGANISM: Homo sapiens

<400> SEQUENCE: 29
tgcttcttaa agaaaaggga aaagaccttt ttctttcttt cagtcttcaa tgattcactg    60
cttcatctcg ctccaccaaa gataaatgaa atctacatct ct                       102

<210> SEQ ID NO 30
<211> LENGTH: 89
<212> TYPE: DNA
<213> ORGANISM: Homo sapiens

<400> SEQUENCE: 30
ctttccccca ctcaasgatt attctaatgt cagagtagaa taaaaaataa gtgcarmgat    60
gctgactctt ccaagcttaa catttctca                                      89

<210> SEQ ID NO 31
<211> LENGTH: 65
<212> TYPE: DNA
<213> ORGANISM: Homo sapiens

<400> SEQUENCE: 31
gggaggaggg cgtgaagggc tgcttgcggt agttgtgtag cagcagcaca atggccgcag    60
acaag                                                                65
```

MULTI-COPY REFERENCE ASSAY

BACKGROUND

Information relating to the copy number of a target of interest in the genome of a biological sample may be desirable for a number of purposes, including basic research and clinical diagnosis of various diseases. One class of diseases where the copy number of a target of interest may be particularly desirable to know is cancer. Numerous cancers present with abnormal copy numbers of one or more genes. In many cases, there exists a positive correlation between copy number and the existence and/or progression of cancer. Therefore, determining the copy number of a target of interest in a sample from a patient of tissue suspected of being cancer tissue may be useful, for example, in diagnosing, treating, and/or monitoring the course of the patient's cancer.

To date, quantitative polymerase chain reaction (qPCR) has been under consideration as a molecular technique for determining copy number of a target of interest. To determine copy number of a target of interest, qPCR may require the simultaneous amplification of both the target of interest and a reference sequence in the genome of the sample. From the relative quantities of the target of interest amplicon and the reference sequence amplicon, the relative copy numbers of the target of interest and the reference sequence can be determined, and assuming the absolute copy number of the reference sequence is known, the copy number of the target of interest may be determined.

However, when attempting to apply qPCR to determine the copy number of a target of interest in a cancer cell, the technique may be rendered difficult as a result of one or both of the random, evolving genomic abnormalities (e.g., aneuploidy) found in cancer cells and the modifications to nucleic acids that may occur when tissue samples are archived by formalin fixing and paraffin embedding (FFPE).

Genomic abnormalities of various types are known to occur in cancer cells, and increase in their quantity, distribution, and complexity as the cancer cells are replicated over time. These genomic abnormalities include gene deletions and multiplications, some of which may be related to a specific function in humans and common to certain cancer types, while others may have no overt effect or association with disease. As a result, a reference sequence of interest may undergo deletion and/or multiplication in the genome of a cancer cell, thereby making it very difficult to determine the absolute copy number of the reference sequence.

Modifications to the nucleic acids (DNA and RNA), such as cross linking of nucleotides to themselves or proteins, depurination of nucleotides, and fragmentation of the nucleic acids are known to occur as part of the archiving of cancer samples by the FFPE method. However, the locations and extent of these modifications are random and vary greatly across FFPE samples, due in large part to one or more factors, such as variability in the sample tissue itself, reagents used in fixation and embedding, and user preferred variations in the FFPE method at different labs. These effects also make it difficult or impossible to determine the absolute copy number of the reference sequence.

Both of these observations provide significant challenges to current molecular genetic assays and tests for DNA level copy number variation, such as qPCR.

Therefore, there exists a need for the selection of reference sequences that are relatively resistant to cancer-induced genomic abnormalities and/or FFPE-induced nucleic acid modifications.

SUMMARY OF THE DISCLOSURE

In one embodiment, the present disclosure relates to a method, comprising quantifying a nucleic acid sequence of interest relative to a reference nucleic acid sequence, wherein at least a first minimum number of copies of the reference nucleic acid sequence is present on each of at least a second minimum number of chromosomes of the genomic DNA of the subject; and determining a copy number of the sequence of interest from the relative quantified amplified sequence of interest.

In some embodiments, the method may further comprise amplifying the nucleic acid sequence of interest in a sample comprising genomic DNA of a subject; and amplifying the reference nucleic acid sequence in the sample; prior to quantifying.

In one embodiment, the reference sequence may have at least 80% sequence identity to at least one portion of genomic DNA comprising from about 60 to about 150 base pairs, wherein the at least one portion is present in chr1-121790-133586, chr1-329448-341534, chr1-648129-660266, chr1-222643865-228172047, chr1-243203764-243215874, chr10-38741930-38753964, chr11-114010-126106, chr16-90239446-90251554, chr19-183944-196032, chr2-114323560-114323652, chr2-243064480-243071940, chr20-62921559-62933673, chr3-197950387-197962431, chr4-119557144-120325498, chr4-165196360-165199636, chr5-180756063-180768074, chr6-170921836-170922549, chr7-39837560-63231088, chr7-128296352-128298474, chr8-143133-150475, chr9-49679-49771, chrY-26424506-27537936, or chr6-132951-145064; the at least one portion is present in at least a first minimum number of copies in the genome; and at least one copy of the at least one portion is present on each of at least a second minimum number of chromosomes.

In a particular embodiment, the reference nucleic acid sequence may have at least 80% sequence identity to at least one of (SEQ ID NO: 1)
GGCTGYTTGCRGTAGTWRTSTRKSWRSMRSMMRMWSRMYGSMSRCARRS

RARRMARWYWSTWDVWAKKMN, (SEQ ID NO: 2)
GGCTGCTTGCAGTAGTTGTGTAGCAGCAGCACAATGGCCGCAGACAAGGA

AAACAGTTTCTAGGAATTCC, (SEQ ID NO: 3)
GGCTGCTTGCGGTAGTTATGTAGCAGCAGCACAATGGCCGCAGACAAGGA

AAACAGTTTCTAGGAATTCC, (SEQ ID NO: 4)
GGCTGCTTGCGGTAGTTGTCTAGCAGCAGCACAATGGCCGCAGACAAGGA

AAACAGTTTCTAGGAATTCC, (SEQ ID NO: 5)
GGCTGCTTGCGGTAGTTGTGTAGCAGCAGCACAATGGCCGCAGACAAGGA

AAACAGTTTCTAAAAATTCC, (SEQ ID NO: 6)
GGCTGCTTGCGGTAGTTGTGTAGCAGCAGCACAATGGCCGCAGACAAGGA

AAACAGTTTCTAGGAATTCC, (SEQ ID NO: 7)
GGCTGCTTGCGGTAGTTGTGTAGCAGCAGCACAATGGCCGCAGACAAGGA
AAACAGTTTCTAGGAATTCN, (SEQ ID NO: 8)
GGCTGTTTGCGGTAGTAGTCTGTGTAGCAGCAGCACAATGGCCGCAGACG
AGGAAAACAGTTTCTAGGAA, (SEQ ID NO: 9)
AGTGCAGYRWTGYTGACTCTTCCAAGCTTAACATTTCTCASAARTCAATT
AGCTTTGTACTGGGAGG, (SEQ ID NO: 10)
AGTGCAGCAATGTTGACTCTTCCAAGCTTAACATTTCTCAGAAGTCAATT
AGCTTTGTACTGGGAGG, (SEQ ID NO: 11)
AGTGCAGCGATGCTGACTCTTCCAAGCTTAACATTTCTCACAAGTCAATT
AGCTTTGTACTGGGAGG, (SEQ ID NO: 12)
AGTGCAGCGTTGCTGACTCTTCCAAGCTTAACATTTCTCACAAATCAATT
AGCTTTGTACTGGGAGG, (SEQ ID NO: 13)
AGTGCAGTGATGCTGACTCTTCCAAGCTTAACATTTCTCACAAGTCAATT
AGCTTTGTACTGGGAGG, (SEQ ID NO: 14)
GTGTAGCAGCAGCACAATGGCCGCAGACAAGGAAAACAGTTTCTAGGAA
TTCCTCGTATATAATTTTATATTTTTGACAAGATTAATGACCCATGCTC
C, (SEQ ID NO: 15)
TGCARMGATGCTGACTCTTCCAAGCTTAACATTTCTCACAAGTCAATTAG
CTTTGTACTGGGAGG, (SEQ ID NO: 16)
TGCTGACTCTTCCAAGCTTAACATTTCTCACAAGTCAATTAGCTTTGTAC
TGGGAGGAGGGCGTGAAGGGCTGCTTGCG, (SEQ ID NO: 17)
CAAGGGACAAGGAAAAATTATCCAAACATTGTTTAAAACAATCATCATTA
ATTAGTAACACTTATCCAGGGGGGTTTTTAACCTTTCCCCCACTCAASGA
TTATTCTAATGTCAGAGTAGAATAAAAAATAAGTGCARMGATGCTGAC, (SEQ ID NO: 18)
GGAGGAGGAAAATAGGTAGTTTTTCAAAAGTTTTCAAAAATATGAAAGA
AGAAATGAAATGGTACTTGGAAGAGATTGTTGAAATGGGAGAGACTATG
GTGGC, (SEQ ID NO: 19)
CAACTAAAAGGCAATGTCACTCCAATAATCACCAGAGTAATCAATTTGCT
TATTGCTGTCCCTTTAAATATAGTTCTCTGG, (SEQ ID NO: 20)
GGAGAGACTATGGTGGCTTGTTTAGAAGCAGTTGAGATAGATCCAATTGA
GATAGAGATATTGAGTATATAAACAAAAGAATGACAAATTAATAGTGTAA
TGGATAACTTGACTTTGGCA, (SEQ ID NO: 21)
GTGTAATGGATAACTTGACTTTGGCAAATATTGTGAATTTTTGTGAAAGT
ACAACTAAAAGGCAATGTCACTCCAATAATCACCAG, (SEQ ID NO: 22)
GTAATCAATTTGCTTATTGCTGTCCCTTTAAATATAGTTCTCTGGTATCA
ACTAACATGTTTTTAACTAATGATGCTTCTTAAAGAAAAGGGAAAAGACC
T, (SEQ ID NO: 23)
CCCTGGGCCCCTCAGGGGAGTCCCTGCTGGACAGTGAGACAGAGAATGAC
CATGATGATGCTTTCCT, (SEQ ID NO: 24)
GGGTTTATGTTTGATATRTAATGTAATTTTCTAATGCTAAATCAAGTGGT
AATTTTGTTAGTCAAGTTGATTTAGTGGCTTGGGAAGAAAGCT, (SEQ ID NO: 25)
GAGACCCCCAGGTGTTGAGGCAGGGCTGGGGTGTCCCCTTCCAACCAGGC
TGTCAAGGCCCCAACTCTGGGGCAGAGGCAGTGGCAGGG, (SEQ ID NO: 26)
CATCCGTTTCACCTGCAGTTGAAGATCCGTGAGGTGCCCAGAAGATCATG
CAGTCAWCAGTCCCACG, (SEQ ID NO: 27)
GAKATAAGGAAGCTCGAGGAAGAGAAAAAACAACTGGAAGGAGAAATC
ATAGATTTTTATAAAATGAMAGCTGCCTCTGAAGC, (SEQ ID NO: 28)
CCGTTTTGGAGGAGGAACAGATTCCATGTCCACTAGAATGGAATGAACAA
GAAATGGAGGAGGAAAATAGGTAGTTTTTCAAAAGTTTTCAAAAATATGA
AAGAAGAAATGAAATGGTACTTGGAAGAGATTGTTGAAATGGGA, (SEQ ID NO: 29)
TGCTTCTTAAAGAAAAGGGAAAAGACCTTTTTCTTTCTTTCAGTCTTCAA
TGATTCACTGCTTCATCTCGCTCCACCAAAGATAAATGAAATCTACATCT
CT, (SEQ ID NO: 30)
CTTTCCCCCACTCAASGATTATTCTAATGTCAGAGTAGAATAAAAAATAA
GTGCARMGATGCTGACTCTTCCAAGCTTAACATTTCTCA,
or (SEQ ID NO: 31)
GGGAGGAGGGCGTGAAGGGCTGCTTGCGGTAGTTGTGTAGCAGCAGCAC
AATGGCCGCAGACAAG.

In another embodiment, the present disclosure relates to a kit, comprising a first probe which specifically hybridizes to at least a portion of at least one reference sequence that has at least 80% sequence identity to at least one portion of genomic DNA comprising from about 60 to about 150 base pairs, wherein the at least one portion is present in chr1-121790-133586, chr1-329448-341534, chr1-648129-660266, chr1-222643865-228172047, chr1-243203764-243215874, chr10-38741930-38753964, chr11-114010-126106, chr16-90239446-90251554, chr19-183944-196032, chr2-114323560-114323652, chr2-243064480-243071940, chr20-62921559-62933673, chr3-197950387-197962431, chr4-119557144-120325498, chr4-165196360-165199636, chr5-180756063-180768074, chr6-170921836-170922549, chr7-39837560-63231088, chr7-128296352-

128298474, chr8-143133-150475, chr9-49679-49771, chrY-26424506-27537936, or chr6-132951-145064; the at least one portion is present in at least a first minimum number of copies in the genome; and at least one copy of the at least one portion is present on each of at least a second minimum number of chromosomes.

In still another embodiment, the present disclosure relates to a composition, comprising a first probe which specifically hybridizes to at least a portion of at least one reference sequence that has at least 80% sequence identity to at least one portion of genomic DNA comprising from about 60 to about 150 base pairs, wherein the at least one portion is present in chr1-121790-133586, chr1-329448-341534, chr1-648129-660266, chr1-222643865-228172047, chr1-243203764-243215874, chr10-38741930-38753964, chr11-114010-126106, chr16-90239446-90251554, chr19-183944-196032, chr2-114323560-114323652, chr2-243064480-243071940, chr20-62921559-62933673, chr3-197950387-197962431, chr4-119557144-120325498, chr4-165196360-165199636, chr5-180756063-180768074, chr6-170921836-170922549, chr7-39837560-63231088, chr7-128296352-128298474, chr8-143133-150475, chr9-49679-49771, chrY-26424506-27537936, or chr6-132951-145064; the at least one portion is present in at least a first minimum number of copies in the genome; and at least one copy of the at least one portion is present on each of at least a second minimum number of chromosomes.

In yet another embodiment, the present disclosure relates to a system, comprising a nucleic acid amplifier configured to amplify a nucleic acid sequence of interest in a sample comprising genomic DNA of a subject and amplify a reference sequence in the sample; a reagent reservoir containing at least a first primer configured to specifically hybridize to a first end of the at least one reference sequence, wherein the reference sequence has at least 80% sequence identity to at least one portion of genomic DNA comprising from about 60 to about 150 base pairs, wherein the at least one portion is present in chr1-121790-133586, chr1-329448-341534, chr1-648129-660266, chr1-222643865-228172047, chr1-243203764-243215874, chr10-38741930-38753964, chr11-114010-126106, chr16-90239446-90251554, chr19-183944-196032, chr2-114323560-114323652, chr2-243064480-243071940, chr20-62921559-62933673, chr3-197950387-197962431, chr4-119557144-120325498, chr4-165196360-165199636, chr5-180756063-180768074, chr6-170921836-170922549, chr7-39837560-63231088, chr7-128296352-128298474, chr8-143133-150475, chr9-49679-49771, chrY-26424506-27537936, or chr6-132951-145064; the at least one portion is present in at least a first minimum number of copies in the genome; and at least one copy of the at least one portion is present on each of at least a second minimum number of chromosomes, and a second primer configured to specifically hybridize to a sequence complementary to a second end of the at least one reference sequence; a detector configured to provide a first indication relating to an amount of the amplified sequence of interest and a second indication relating to an amount of the amplified reference sequence; and a controller configured to quantify the amplified sequence of interest relative to the amplified reference sequence, based at least in part on the first indication and the second indication and determine a copy number of the sequence of interest from the relative quantified amplified sequence of interest.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein.

FIG. 1A shows the decimal point calculated copy number of IRS2 as determined by qPCR with an RNaseP reference assay.

FIG. 1B shows the rounded copy number of IRS2 as determined by qPCR with an RNaseP reference assay.

FIG. 2A shows the decimal point calculated copy number of IRS2 as determined by qPCR with a reference assay based on SEQ ID NO:1-8.

FIG. 2B shows the rounded copy number of IRS2 as determined by qPCR with a reference assay based on SEQ ID NO:1-8.

DESCRIPTION

Figure 3A:
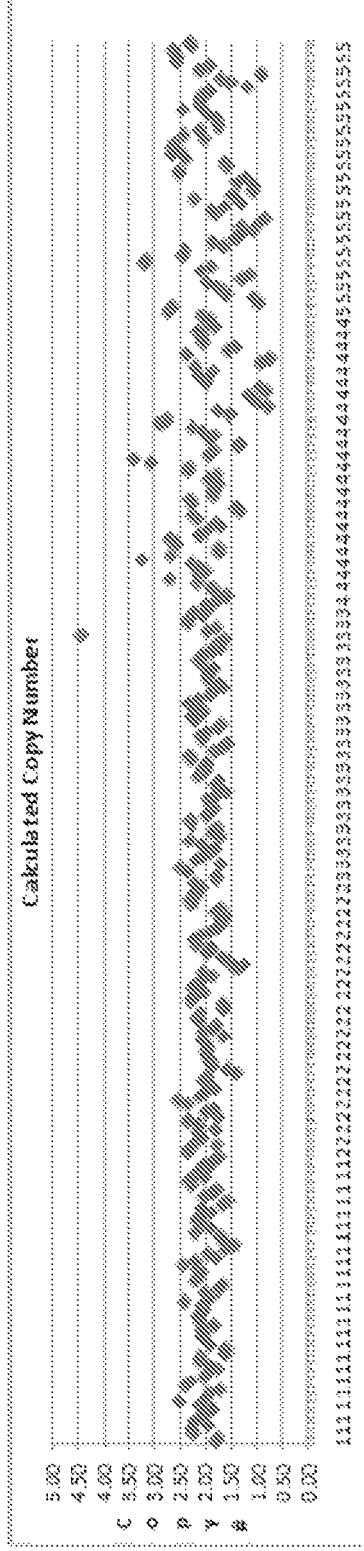
FIG. 3A shows the decimal point calculated copy number of IRS2 as determined by qPCR with a reference assay based on SEQ ID NO:9-13.

Various embodiments of the present disclosure provide reference sequences that are relatively resistant to cancer-induced genomic abnormalities and/or FFPE-induced nucleic acid modifications. More specifically, the disclosure provides target sequences in the genome that are repeated multiple times, across many chromosomes, and demonstrate substantially normal copy number and resistance to severe modifications and fragmentation, even in cancer cells subjected to FFPE.

In one embodiment, the present disclosure relates to a method, comprising amplifying a nucleic acid sequence of interest in a sample comprising genomic DNA of a subject; amplifying a reference nucleic acid sequence in the sample, wherein at least one copy of the reference nucleic acid sequence is present on each of at least ten chromosomes of the genomic DNA of the subject; quantifying the amplified sequence of interest relative to the amplified reference sequence; and determining a copy number of the sequence of interest from the relative quantified amplified sequence of interest.

Amplifying may be performed by any technique known to the person of ordinary skill in the art. Desirably, amplifying may be performed by a technique which permits quantification of the sequence of interest relative to the reference sequence. Exemplary techniques include, but are not limited to, polymerase chain reaction (PCR) (Saiki et al. (1985) Science 230: 1350), quantitative real-time PCR (qPCR), digital PCR, ligase chain reaction (LCR) (Landegren et al. (1988) Science 241:1077-1080), helicase-dependent amplification (HDA) (Vincent et al. (2004) EMBO rep 5(8):795-800), thermostable HDA (tHDA) (An et al. (2005) J Biol Chem 280 (32):28952-28958), strand displacement amplification (SDA) (Walker et al. (1992) Nucleic Acids Res 20(7):16916), multiple displacement amplification (MDA) (Dean et al. (2002) Proc Natl Acad Sci USA 99(8): 5261-5266), rolling circle amplification (RCA) (Liu et al. (1996) J Am Chem Soc 118:1587-1594), restriction aided RCA (Wang et al. (2004) Genome Res 14:2357-2366), single primer isothermal amplification (SPIA) (Daffom et al. (2004) Biotechniques 37(5):854-7), transcription mediated amplification (TMA) (Vuorinen et al. (1995) J Clin Microbiol 33: 1856-1859), nicking enzyme amplification reaction (NEAR) (Maples et al. US2009017453), exponential amplification reaction (EXPAR) (Van Ness et al. (2003) Proc Natl Acad Sci USA 100 (8):4504-4509), loop mediated isothermal amplification (LAMP) (Notomi et al. (2000) Nucleic Acids Res 28(12):e63), recombinase polymerase amplification (RPA) (Piepenburg et al. (2006) PloS BioI 4(7): 1115-1120), nucleic acid sequence based amplification (NASBA) (Kievits et al. (1991) J Virol Methods 35:273-286), smart-amplification process (SMAP) (Mitani et al. (2007) Nat Methods 4(3):257-62), nanostring amplification (Geiss et al (2008) Nature Biotechnology 26:317-325; Schwanhausser et al (2011) Nature 473:337-342; commercially available as the nCounter® platform from NanoString Technologies, Seattle, Wash.), or next generation sequencing (NGS) (Rothberg et al (2011) Nature 475:348-352; Metzker M (2010) Nature Rev Genetics 11:31-46).

In a particular embodiment, amplification is performed by TaqMan quantitative polymerase chain reaction (qPCR).

Generally, qPCR platform assays use two genome targets together to determine the copy number of a gene or region of the genome in a test sample. One of the genome targets is a qPCR assay for the target of interest (TOI), and the second is a qPCR reference assay for what is assumed to be a normal, unmodified region of the genome. The two assays are run simultaneously and in parallel on the same test sample. After one or more cycles of the polymerase chain reaction, the Cq values of each assay (indicative of the relative amount of TOI or reference amplicon) may be determined by techniques known to the person of ordinary skill in the art and/or described in more detail below, and a delta Cq between them is calculated. This calculated delta Cq may then be compared to a delta Cq that is representative of a known copy number for the TOI. For example, the representative delta Cq may be a delta Cq determined from a sample known to be normal (i.e., having a copy number of 2, one copy from each of a pair of chromosomes). This final calculated delta delta Cq between test sample and known sample/value may then be transformed into a decimal number or an integer number representing the copy number of the gene or region of genome in the test sample.

For reasons described above, the challenge in cancer FFPE samples is in the ability to find a reference genome target (qPCR reference assay target) that is both normal and relatively unmodified by fixation and embedding. Additionally or alternatively, for some samples the ability to find a reference genome target may be complicated by a particular disease state, which includes but is not limited to cancer, where a potential reference genomic target may be altered by the disease state and is itself multiplied relative to its typical population.

Any nucleic acid sequence from the genomic DNA of a subject and of interest to the user of the method may be amplified and quantified according to the method. For example, the sequence of interest may be at least a portion of a gene which has an association with a disease. As will be apparent to the person of ordinary skill in the art, the sample may be any tissue likely or possibly containing the nucleic acid sequence of interest in genomic DNA.

The method may be used to amplify and quantify a sequence of interest from tissue suspected of being cancer tissue, including tissue which has been subjected to formalin fixing and paraffin embedding (FFPE) prior to the amplifying the sequence of interest and amplifying the reference sequence. In such a use, the sequence of interest may be at least a portion of a gene for which there exists a correlation between the gene's copy number and the presence and/or stage of a cancer.

Any reference nucleic acid sequence known or expected to be present in the genomic DNA of the sample may be amplified. However, a person of ordinary skill in the art will be aware that in many embodiments, such as those in which the sample is suspected of being cancer tissue, and especially a sample previously subject to FFPE, any particular locus of a copy of a reference nucleic acid sequence may have undergone a recombination event, an aneuploidy event, or the like. Thus, the number of copies of the reference sequence in the sample may differ from that expected by simple counting of the number of loci of the reference sequence in a non-diseased sample from the subject or a member of the subject's species.

Therefore, it is desirable that the sample comprises at least one copy of the reference nucleic acid sequence on each of at least ten chromosomes of the genomic DNA of the subject. The presence of multiple, physically dispersed copies of the reference sequence may smooth or average out the effects of individual disruptions or duplications of various loci.

In one embodiment, the reference sequence has at least 80% sequence identity to at least one portion of genomic DNA comprising from about 60 to about 150 base pairs, wherein the at least one portion is present in chr1-121790-133586, chr1-329448-341534, chr1-648129-660266, chr1-222643865-228172047, chr1-243203764-243215874, chr10-38741930-38753964, chr11-114010-126106, chr16-90239446-90251554, chr19-183944-196032, chr2-114323560-114323652, chr2-243064480-243071940, chr20-62921559-62933673, chr3-197950387-197962431, chr4-119557144-120325498, chr4-165196360-165199636, chr5-180756063-180768074, chr6-170921836-170922549, chr7-39837560-63231088, chr7-128296352-128298474, chr8-143133-150475, chr9-49679-49771, chrY-26424506-27537936, or chr6-132951-145064; the at least one portion is present in at least a first minimum number of copies in the genome; and at least one copy of the at least one portion is present on each of at least a second minimum number of chromosomes.

In one embodiment, the first minimum number may be 5, 6, 7, 8, 9, 10, 11, 12, 13, 14, or 15 copies. Independently, the second minimum number may be 5, 6, 7, 8, 9, 10, or 11 chromosomes. The first and second minimum numbers may be enumerated, estimated, or predicted based on any available human reference genome.

In a particular embodiment, the reference sequence has at least 80% sequence identity to at least one of

```
                                              (SEQ ID NO: 1)
GGCTGYTTGCRGTAGTWRTSTRKSWRSMRSMMRMWSRMYGSMSRCARRS

RARRMARWYWSTWDVWAKKMN, (SEQ ID NO: 2)
GGCTGCTTGCAGTAGTTGTGTAGCAGCAGCACAATGGCCGCAGACAAGGA

AAACAGTTTCTAGGAATTCC, (SEQ ID NO: 3)
GGCTGCTTGCGGTAGTTATGTAGCAGCAGCACAATGGCCGCAGACAAGGA

AAACAGTTTCTAGGAATTCC, (SEQ ID NO: 4)
GGCTGCTTGCGGTAGTTGTCTAGCAGCAGCACAATGGCCGCAGACAAGGA

AAACAGTTTCTAGGAATTCC,
```

(SEQ ID NO: 5)
GGCTGCTTGCGGTAGTTGTGTAGCAGCAGCACAATGGCCGCAGACAAGGA
AAACAGTTTCTAAAAATTCC, (SEQ ID NO: 6)
GGCTGCTTGCGGTAGTTGTGTAGCAGCAGCACAATGGCCGCAGACAAGGA
AAACAGTTTCTAGGAATTCC, (SEQ ID NO: 7)
GGCTGCTTGCGGTAGTTGTGTAGCAGCAGCACAATGGCCGCAGACAAGGA
AAACAGTTTCTAGGAATTCN, (SEQ ID NO: 8)
GGCTGTTTGCGGTAGTAGTCTGTGTAGCAGCAGCACAATGGCCGCAGACG
AGGAAAACAGTTTCTAGGAA, (SEQ ID NO: 9)
AGTGCAGYRWTGYTGACTCTTCCAAGCTTAACATTTCTCASAARTCAATT
AGCTTTGTACTGGGAGG, (SEQ ID NO: 10)
AGTGCAGCAATGTTGACTCTTCCAAGCTTAACATTTCTCAGAAGTCAATT
AGCTTTGTACTGGGAGG, (SEQ ID NO: 11)
AGTGCAGCGATGCTGACTCTTCCAAGCTTAACATTTCTCACAAGTCAATT
AGCTTTGTACTGGGAGG, (SEQ ID NO: 12)
AGTGCAGCGTTGCTGACTCTTCCAAGCTTAACATTTCTCACAAATCAATT
AGCTTTGTACTGGGAGG, (SEQ ID NO: 13)
AGTGCAGTGATGCTGACTCTTCCAAGCTTAACATTTCTCACAAGTCAATT
AGCTTTGTACTGGGAGG, (SEQ ID NO: 14)
GTGTAGCAGCAGCACAATGGCCGCAGACAAGGAAAACAGTTTCTAGGAA
TTCCTCGTATATAATTTTATATTTTTGACAAGATTAATGACCCATGCTC
C, (SEQ ID NO: 15)
TGCARMGATGCTGACTCTTCCAAGCTTAACATTTCTCACAAGTCAATTAG
CTTTGTACTGGGAGG, (SEQ ID NO: 16)
TGCTGACTCTTCCAAGCTTAACATTTCTCACAAGTCAATTAGCTTTGTAC
TGGGAGGAGGGCGTGAAGGGCTGCTTGCG, (SEQ ID NO: 17)
CAAGGGACAAGGAAAAATTATCCAAACATTGTTTAAAACAATCATCATTA
ATTAGTAACACTTATCCAGGGGGGTTTTTAACCTTTCCCCCACTCAASGA
TTATTCTAATGTCAGAGTAGAATAAAAAATAAGTGCARMGATGCTGAC, (SEQ ID NO: 18)
GGAGGAGGAAAATAGGTAGTTTTTCAAAAGTTTTCAAAAATATGAAAAGA
AGAAATGAAATGGTACTTGGAAGAGATTGTTGAAATGGGAGAGACTATG
GTGGC, (SEQ ID NO: 19)
CAACTAAAAGGCAATGTCACTCCAATAATCACCAGAGTAATCAATTTGCT
TATTGCTGTCCCTTTAAATATAGTTCTCTGG, (SEQ ID NO: 20)
GGAGAGACTATGGTGGCTTGTTTAGAAGCAGTTGAGATAGATCCAATTGA
GATAGAGATATTGAGTATATAAACAAAAGAATGACAAATTAATAGTGTAA
TGGATAACTTGACTTTGGCA, (SEQ ID NO: 21)
GTGTAATGGATAACTTGACTTTGGCAAATATTGTGAATTTTTGTGAAAGT
ACAACTAAAAGGCAATGTCACTCCAATAATCACCAG, (SEQ ID NO: 22)
GTAATCAATTTGCTTATTGCTGTCCCTTTAAATATAGTTCTCTGGTATCA
ACTAACATGTTTTTAACTAATGATGCTTCTTAAAGAAAAGGGAAAAGACC
T, (SEQ ID NO: 23)
CCCTGGGCCCCTCAGGGGAGTCCCTGCTGGACAGTGAGACAGAGAATGAC
CATGATGATGCTTTCCT, (SEQ ID NO: 24)
GGGTTTATGTTTGATATRTAATGTAATTTTCTAATGCTAAATCAAGTGGT
AATTTTGTTAGTCAAGTTGATTTAGTGGCTTGGGAAGAAAGCT, (SEQ ID NO: 25)
GAGACCCCCAGGTGTTGAGGCAGGGCTGGGGTGTCCCCTTCCAACCAGGC
TGTCAAGGCCCCAACTCTGGGGCAGAGGCAGTGGCAGGG, (SEQ ID NO: 26)
CATCCGTTTCACCTGCAGTTGAAGATCCGTGAGGTGCCCAGAAGATCATG
CAGTCAWCAGTCCCACG, (SEQ ID NO: 27)
GAKATAAGGAAGCTCGAGGAAGAGAAAAAACAACTGGAAGGAGAAATC
ATAGATTTTTATAAAATGAMAGCTGCCTCTGAAGC, (SEQ ID NO: 28)
CCGTTTTGGAGGAGGAACAGATTCCATGTCCACTAGAATGGAATGAACAA
GAAATGGAGGAGGAAAATAGGTAGTTTTTCAAAAGTTTTCAAAAATATGA
AAAGAAGAAATGAAATGGTACTTGGAAGAGATTGTTGAAATGGGA, (SEQ ID NO: 29)
TGCTTCTTAAAGAAAAGGGAAAAGACCTTTTTCTTTCTTTCAGTCTTCAA
TGATTCACTGCTTCATCTCGCTCCACCAAAGATAAATGAAATCTACATCT
CT, (SEQ ID NO: 30)
CTTTCCCCCACTCAASGATTATTCTAATGTCAGAGTAGAATAAAAAATAA
GTGCARMGATGCTGACTCTTCCAAGCTTAACATTTCTCA,
or (SEQ ID NO: 31)
GGGAGGAGGGCGTGAAGGGCTGCTTGCGGTAGTTGTGTAGCAGCAGCAC
AATGGCCGCAGACAAG.

In one embodiment, the reference sequence has at least 80% sequence identity to at least one of SEQ ID NO:1-8.

In one embodiment, the reference sequence has at least 80% sequence identity to at least one of SEQ ID NO:9-13.

A first set of sequences, SEQ ID NO:1-8, correspond to sequences found in the human genome at chr1:121836-121905, chr1:243203810-243203879, chr1:341419+341488, chr1:648175-648244, chr2:243071825+243071894, chr3:197962362+197962431, chr4: 119569113+119569182, chr5:180768034+180768103, chr6:

132997-133066, chr6:170922434+170922503, chr10: 38753924+38753993, chr11:114056-114125, chr16: 90251439+90251508, chr19:183990-184059, chr20: 62933558+62933627, chrUn_g1000227:58864-58933, chrY:26436540+26436609, and chrY:27525831-27525900.

A second set of sequences, SEQ ID NO:9-13, correspond to sequences found in the human genome at chr1: 224126101-224126167, chr1:228152189+228152255, chr1: 243203891-243203957, chr1:341341+341407, chr1: 648256-648322, chr2:243071747+243071813, chr3: 197962284+197962350, chr4:119569035+119569101, chr5:180767956+180768022, chr6:133078-133144, chr6: 170922356+170922422, chr8:143260-143326, chr10: 38753846+38753912, chr11:114137-114203, chr16: 90251361+90251427, chr19:184071-184137, chr20: 62933480+62933546, and chrUn_g1000227:58945-59011.

In any nucleic acid sequence listing herein, the standard IUPAC table of naturally-occurring and degenerate nucleotides is used:

| Symbol | Description | Bases represented |
|--------|-------------|-------------------|
| A | adenine | A |
| C | cytosine | C |
| G | guanine | G |
| T | thymine | T |
| U | uracil | U |
| W | Weak | A, T |
| S | Strong | C, G |
| M | Amino | A, C |
| K | Keto | G, T |
| R | Purine | A, G |
| Y | Pyrimidine | C, T |
| B | Not adenine | C, G, T |
| D | Not cytosine | A, G, T |
| H | Not guanine | A, C, T |
| V | Not thymine | A, C, G |
| N | Any base (not a gap) | A, C, G, T |

Though not to be bound by theory, the present inventor has found that each of the first set and the second set of sequences are both highly repeated (~20 copies in the human genome), physically dispersed throughout the human genome, and relatively more resistant to disruption and/or duplication by FFPE than typical genomic DNA sequences. As a result, a sequence having at least 80% identity to one or more of SEQ ID NO:1-13 may be particularly suitable as a reference sequence, especially in samples suspected of being cancer tissue, particular FFPE-processed tissue.

The amplifying steps yield an amplified sequence of interest and an amplified reference sequence. Generally, so long as performance of the amplifying steps is synchronized and amplification has not proceeded to an extent where the quantity of any reagent other than the amplified sequence of interest and the amplified reference sequence is rate-limiting, at any point, the relative amounts of the amplified sequence of interest and the amplified reference sequence will be proportional to their copy number in the genomic DNA of the sample.

Thus, the method may comprise quantifying the amplified sequence of interest relative to the amplified reference sequence. The quantifying may be performed by any technique known to the person of ordinary skill in the art. For example, by the use of two probes, each comprising a fluorescent moiety at a first end and a quencher for that fluorescent moiety at a second end, with one probe specifically hybridizing to the sequence of interest and the other specifically hybridizing to the reference sequence, in TaqMan qPCR, cleavage of the quencher by the action of Taq polymerase will generate a fluorescence signal proportional to the amount of probe hybridized to the sequence of interest or the reference sequence. Thus, in a simple hypothetical non-limiting example, if the fluorescence signal from the probe hybridizing to the reference sequence is five times more intense than the fluorescence signal from the probe hybridizing to the sequence of interest, the relative quantity of the amplified sequence of interest would be 0.2. (As will be apparent to the person of ordinary skill in the art, alternative mathematically equivalent expressions may be used to arrive at a relative quantity).

In some embodiments, amplification of the TOI and the reference sequence may be omitted. Techniques for quantifying non-amplified nucleic acid sequences are known to the person of ordinary skill in the art.

The measure of relative quantitation may be reported using the term "fold change", which refers to the amount of amplified product (which relates to the copy number) in the sequence of interest relative to that of the reference genome target. Fold change can be quantified using any of several available methods, including but not limited to those described by Livak, et al. (Methods, 25:402-408 (2001)), commercially available products such as CopyCaller™ (Applied Biosystems), or any other suitable algorithm for comparing amounts of fluorescence signals. In many embodiments, fold change is determined by comparing the $C_T$ of the sequence of interest to the $C_T$ of the reference genome target. Some suitable algorithms include but are not limited to, the methods described in U.S. application Ser. No. 13/107,786, "Karyotyping Assay" filed on May 13, 2011, the disclosure of which is hereby incorporated by reference in its entirety.

The quantifying step yields a relative quantified amplified sequence of interest. The method may then comprise determining a copy number of the sequence of interest from the relative quantified amplified sequence of interest. Determining requires an indication of the copy number of the reference sequence. Such an indication may be provided by analysis of the genome of a non-diseased sample from the subject or one or more members of the subject's species. This technique may be especially suitable, regarding samples suspected of being cancer tissue, for a reference sequence that is one or more of highly repeated, physically dispersed, and relatively resistant to disruption and/or duplication by FFPE. For example, the copy number of a reference sequence having at least 80% identity to one or more of SEQ ID NO:1-13 in a non-diseased sample may be expected to be substantially equal to the copy number of the reference sequence in a sample suspected of being cancer tissue.

Continuing the simple hypothetical non-limiting example begun above, if the copy number of the reference sequence is 20, then the copy number of the amplified sequence of interest may be determined to be 20*0.2=4. (As should be apparent, this is a simple probe-based example of a copy number calculation. It is a routine matter for the person of ordinary skill in the art, having the benefit of the present disclosure, to perform copy number calculation for other assay techniques, such as qPCR.)

The determined copy number of the sequence of interest may be used for any purpose which would commend itself to the person of ordinary skill in the art. In a particular embodiment, the method may further comprise diagnosing the subject as having a cancer-related biomarker, based on the sequence of interest being associated with the cancer and the copy number being indicative of the cancer.

In one embodiment, the present disclosure relates to a kit comprising a first probe which specifically hybridizes to at least a portion of at least one reference sequence having at least 80% sequence identity to at least one portion of genomic DNA comprising from about 60 to about 150 base pairs, wherein the at least one portion is present in chr1-121790-133586, chr1-329448-341534, chr1-648129-660266, chr1-222643865-228172047, chr1-243203764-243215874, chr10-38741930-38753964, chr11-114010-126106, chr16-90239446-90251554, chr19-183944-196032, chr2-114323560-114323652, chr2-243064480-243071940, chr20-62921559-62933673, chr3-197950387-197962431, chr4-119557144-120325498, chr4-165196360-165199636, chr5-180756063-180768074, chr6-170921836-170922549, chr7-39837560-63231088, chr7-128296352-128298474, chr8-143133-150475, chr9-49679-49771, chrY-26424506-27537936, or chr6-132951-145064; the at least one portion is present in at least a first minimum number of copies in the genome; and at least one copy of the at least one portion is present on each of at least a second minimum number of chromosomes.

In a particular embodiment, the reference sequence has at least 80% sequence identity to at least one of SEQ ID NO:1-31.

In a more particular embodiment, the reference sequence has at least 80% sequence identity to at least one of SEQ ID NO:1-13.

A "probe," as used herein, refers to a compound comprising a nucleic acid sequence and a detectable moiety. As such, and for the avoidance of doubt, any "probe" referred to herein is non-naturally occurring.

In one embodiment, the first probe comprises a nucleic acid sequence configured to specifically hybridize to at least the portion of the at least one reference sequence, a fluorescent reporter at a first end of the nucleic acid sequence, and a fluorescent quencher at a second end of the nucleic acid sequence.

In a further embodiment, the nucleic acid sequence is configured to specifically hybridize to the entirety of at least one reference sequence.

A percentage of sequence identity can be determined by any technique known to the person of ordinary skill in the art. In some embodiments, the reference sequence has at least 81%, 82%, 83%, 84%, 85%, 86%, 87%, 88%, 89%, 90%, 91%, 92%, 93%, 94%, 95%, 96%, 97%, 98%, 99%, 99.5%, or 99.9% sequence identity to at least one of SEQ ID NO:1-13.

By use of techniques known to the person of ordinary skill in the art, the first probe may allow the detection of at least the portion of the at least one reference sequence.

In addition to the first probe, the kit may comprise other components. For example, the kit may further comprise a first primer configured to specifically hybridize to a first end of the at least one reference sequence, and a second primer configured to specifically hybridize to a sequence complementary to a second end of the at least one reference sequence.

By "primers" is meant nucleic acid molecules which, in the presence of the at least one reference sequence and other reagent(s), may allow amplification of the at least one reference sequence.

Alternatively or in addition, the kit may further comprise a second probe which specifically hybridizes to at least a portion of at least one nucleic acid sequence of interest. Other than the sequence to which it specifically hybridizes, the second probe may have the same characteristics as the first probe described above.

Any nucleic acid sequence of interest may be the hybridization target of the second probe. In one embodiment, the sequence of interest is a portion or the entirety of a gene associated with a cancer.

Alternatively or in addition, the kit may further comprise a third primer configured to specifically hybridize to a first end of the at least one nucleic acid sequence of interest, and a fourth primer configured to specifically hybridize to a sequence complementary to a second end of the at least one nucleic acid sequence of interest. In one embodiment, the present disclosure relates to a composition, comprising a first probe which specifically hybridizes to at least a portion of at least one reference sequence having at least 80% sequence identity to at least one portion of genomic DNA comprising from about 60 to about 150 base pairs, wherein the at least one portion is present in chr1-121790-133586, chr1-329448-341534, chr1-648129-660266, chr1-222643865-228172047, chr1-243203764-243215874, chr10-38741930-38753964, chr11-114010-126106, chr16-90239446-90251554, chr19-183944-196032, chr2-114323560-114323652, chr2-243064480-243071940, chr20-62921559-62933673, chr3-197950387-197962431, chr4-119557144-120325498, chr4-165196360-165199636, chr5-180756063-180768074, chr6-170921836-170922549, chr7-39837560-63231088, chr7-128296352-128298474, chr8-143133-150475, chr9-49679-49771, chrY-26424506-27537936, or chr6-132951-145064; the at least one portion is present in at least a first minimum number of copies in the genome; and at least one copy of the at least one portion is present on each of at least a second minimum number of chromosomes.

In a particular embodiment, the reference sequence has at least 80% sequence identity to at least one of SEQ ID NO:1-31.

In a more particular embodiment, the reference sequence has at least 80% sequence identity to at least one of SEQ ID NO:1-13.

The first probe may be substantially the same as the first probe of the kit, described above.

The composition may further comprise one or more of (i) a first primer configured to specifically hybridize to a first end of at least one reference sequence, and a second primer configured to specifically hybridize to a sequence complementary to a second end of at least one reference sequence; (ii) a second probe which specifically hybridizes to at least a portion of at least one nucleic acid sequence of interest; or (iii) a third primer configured to specifically hybridize to a first end of at least one nucleic acid sequence of interest, and a fourth primer configured to specifically hybridize to a sequence complementary to a second end of at least one nucleic acid sequence of interest, substantially the same as the corresponding further component(s) of the kit, described above.

In one embodiment, the present disclosure relates to a system, comprising:

a nucleic acid amplifier configured to amplify a nucleic acid sequence of interest in a sample comprising genomic DNA of a subject and amplify a reference sequence in the sample;

a reagent reservoir containing at least a first primer configured to specifically hybridize to a first end of at least one reference sequence, wherein the reference sequence has at least 80% sequence identity to at least one portion of genomic DNA comprising from about 60 to about 150 base pairs, wherein the at least one portion is present in chr1-121790-133586, chr1-329448-341534, chr1-648129-660266, chr1-222643865-228172047, chr1-243203764-

243215874, chr10-38741930-38753964, chr11-114010-126106, chr16-90239446-90251554, chr19-183944-196032, chr2-114323560-114323652, chr2-243064480-243071940, chr20-62921559-62933673, chr3-197950387-197962431, chr4-119557144-120325498, chr4-165196360-165199636, chr5-180756063-180768074, chr6-170921836-170922549, chr7-39837560-63231088, chr7-128296352-128298474, chr8-143133-150475, chr9-49679-49771, chrY-26424506-27537936, or chr6-132951-145064; the at least one portion is present in at least a first minimum number of copies in the genome; and at least one copy of the at least one portion is present on each of at least a second minimum number of chromosomes, and a second primer configured to specifically hybridize to a sequence complementary to a second end of at least one reference sequence;

a detector configured to provide a first indication relating to an amount of the amplified sequence of interest and a second indication relating to an amount of the amplified reference sequence; and a controller configured to quantify the amplified sequence of interest relative to the amplified reference sequence, based at least in part on the first indication and the second indication; and determine a copy number of the sequence of interest from the relative quantified amplified sequence of interest.

Nucleic acid amplifiers are known to the person of ordinary skill in the art. Generally, nucleic acid amplifiers use one or more primers and one or more chemical or enzymatic agents to copy a template nucleic acid sequence, such as a sequence of interest or a reference sequence. Such copying can be cycled multiple times to yield relatively large amounts of the sequence of interest and the reference sequence. Desirably, the nucleic acid amplifier is configured to amplify the sequence of interest and the reference sequence simultaneously and in parallel, e.g., by adding different sets of primers, one specific to the sequence of interest and the other specific to the reference sequence, to otherwise identical reaction solutions, such as in different wells of a multi-well plate.

The system also comprises a reagent reservoir. Generally, the reagent reservoir contains materials required for the amplification reaction to occur, such as primers, chemical or enzymatic agents, free nucleotides incorporable into copies of template sequences, etc. The reagent reservoir may also contain one or more probes or other compounds comprising detectable moieties. Any of these materials may be stored separately and/or two or more thereof may be combined for storage in the reagent reservoir. These materials are generally in aqueous solution and can be introduced to reaction solution(s) by techniques known to the person of ordinary skill in the art. Such introduction can occur once or multiple times before, during, or after an amplification process. For example, some reagent(s) may be added once per amplification cycle.

In one embodiment, the reagent reservoir containing at least a first primer configured to specifically hybridize to a first end of the at least one reference sequence, wherein the reference sequence has at least 80% sequence identity to at least one of SEQ ID NO:1-31, such as SEQ ID NO:1-13, and a second primer configured to specifically hybridize to a sequence complementary to a second end of the at least one reference sequence.

The reference sequence, the determination of a sequence identity percentage, and SEQ ID NO:1-38 are described elsewhere herein.

The system also comprises a detector. Generally, the detector may be configured to detect a probe for the sequence of interest, the reference sequence, or both. Upon detection, the detector may perform various signal processing and/or analysis operations to provide a first indication relating to an amount of the amplified sequence of interest and a second indication relating to an amount of the amplified reference sequence.

The system also comprises a controller. The controller may be configured to quantify the amplified sequence of interest relative to the amplified reference sequence, based at least in part on the first indication and the second indication; and determine a copy number of the sequence of interest from the relative quantified amplified sequence of interest. It may store the determined copy number in a memory, display it to a user, write it to a computer-readable file, or the like.

In a further embodiment, the controller may be configured to diagnose the subject as having a cancer-related biomarker, based on the sequence of interest being associated with the cancer and the copy number being indicative of the cancer.

Although the nucleic acid amplifier, the reagent reservoir, the detector, and the controller have been described separately above, any two or more thereof may be components of a single apparatus.

In certain embodiments, the disclosure provides:

1. A method, comprising: amplifying a nucleic acid sequence of interest in a sample comprising genomic DNA of a subject; amplifying a reference sequence in the sample, wherein the reference sequence has at least 80% sequence identity to at least one portion of genomic DNA comprising from about 60 to about 150 base pairs, wherein the at least one portion is present in chr1-121790-133586, chr1-329448-341534, chr1-648129-660266, chr1-222643865-228172047, chr1-243203764-243215874, chr10-38741930-38753964, chr11-114010-126106, chr16-90239446-90251554, chr19-183944-196032, chr2-114323560-114323652, chr2-243064480-243071940, chr20-62921559-62933673, chr3-197950387-197962431, chr4-119557144-120325498, chr4-165196360-165199636, chr5-180756063-180768074, chr6-170921836-170922549, chr7-39837560-63231088, chr7-128296352-128298474, chr8-143133-150475, chr9-49679-49771, chrY-26424506-27537936, or chr6-132951-145064; the at least one portion is present in at least a first minimum number of copies in the genome; and at least one copy of the at least one portion is present on each of at least a second minimum number of chromosomes; quantifying the amplified sequence of interest relative to the amplified reference sequence; and determining a copy number of the sequence of interest from the relative quantified amplified sequence of interest.

2. In the method, the reference sequence can have at least 80% sequence identity to at least one of SEQ ID NOs: 1-31.

3. In the method, the reference sequence can have at least 80% sequence identity to at least one of SEQ ID NO:1-13.

4. In the method, the sample can include tissue suspected of being cancer tissue.

5. In the method, the sample has been subjected to formalin fixing and paraffin embedding (FFPE) prior to amplifying the sequence of interest and amplifying the reference sequence.

6. The method can also include: diagnosing the subject as having a cancer-related biomarker, based on the sequence of interest being associated with the cancer and the copy number being indicative of the cancer.

7. In the method, amplifying the sequence of interest and amplifying the reference sequence can be performed by TaqMan quantitative polymerase chain reaction (qPCR).

8. A kit, comprising: a first probe which specifically hybridizes to at least a portion of at least one reference sequence having at least 80% sequence identity to at least one portion of genomic DNA comprising from about 60 to about 150 base pairs, wherein the at least one portion is present in chr1-121790-133586, chr1-329448-341534, chr1-648129-660266, chr1-222643865-228172047, chr1-243203764-243215874, chr10-38741930-38753964, chr11-114010-126106, chr16-90239446-90251554, chr19-183944-196032, chr2-114323560-114323652, chr2-243064480-243071940, chr20-62921559-62933673, chr3-197950387-197962431, chr4-119557144-120325498, chr4-165196360-165199636, chr5-180756063-180768074, chr6-170921836-170922549, chr7-39837560-63231088, chr7-128296352-128298474, chr8-143133-150475, chr9-49679-49771, chrY-26424506-27537936, or chr6-132951-145064; the at least one portion is present in at least a first minimum number of copies in the genome; and at least one copy of the at least one portion is present on each of at least a second minimum number of chromosomes 9. In the kit, the reference sequence can have at least 80% sequence identity to at least one of SEQ ID NO:1-31.

10. In the kit, the reference sequence can have at least 80% sequence identity to at least one of SEQ ID NO:1-13.

11. In the kit, the first probe can include a nucleic acid sequence configured to specifically hybridize to at least the portion of the at least one reference sequence, a fluorescent reporter at a first end of the nucleic acid sequence, and a fluorescent quencher at a second end of the nucleic acid sequence.

12. The kit can further include: a first primer configured to specifically hybridize to a first end of the at least one reference sequence, and a second primer configured to specifically hybridize to a sequence complementary to a second end of the at least one reference sequence.

13. The kit can further include: a second probe which specifically hybridizes to at least a portion of at least one nucleic acid sequence of interest.

14. The kit can further include: a third primer configured to specifically hybridize to a first end of the at least one nucleic acid sequence of interest, and a fourth primer configured to specifically hybridize to a sequence complementary to a second end of the at least one nucleic acid sequence of interest.

15. A composition that includes: a first probe which specifically hybridizes to at least a portion of at least one reference sequence having at least 80% sequence identity to at least one portion of genomic DNA comprising from about 60 to about 150 base pairs, wherein the at least one portion is present in chr1-121790-133586, chr1-329448-341534, chr1-648129-660266, chr1-222643865-228172047, chr1-243203764-243215874, chr10-38741930-38753964, chr11-114010-126106, chr16-90239446-90251554, chr19-183944-196032, chr2-114323560-114323652, chr2-243064480-243071940, chr20-62921559-62933673, chr3-197950387-197962431, chr4-119557144-120325498, chr4-165196360-165199636, chr5-180756063-180768074, chr6-170921836-170922549, chr7-39837560-63231088, chr7-128296352-128298474, chr8-143133-150475, chr9-49679-49771, chrY-26424506-27537936, or chr6-132951-145064; the at least one portion is present in at least a first minimum number of copies in the genome; and at least one copy of the at least one portion is present on each of at least a second minimum number of chromosomes.

16. In the composition, the reference sequence can have at least 80% sequence identity to at least one of SEQ ID NO:1-31.

17. In the composition, the reference sequence can have at least 80% sequence identity to at least one of SEQ ID NO:1-13.

18. In the composition, the first probe can include a nucleic acid sequence configured to specifically hybridize to at least the portion of the at least one reference sequence, a fluorescent reporter at a first end of the nucleic acid sequence, and a fluorescent quencher at a second end of the nucleic acid sequence.

19. The composition can further include: a first primer configured to specifically hybridize to a first end of the at least one reference sequence, and a second primer configured to specifically hybridize to a sequence complementary to a second end of the at least one reference sequence.

20. The composition can further include: a second probe which specifically hybridizes to at least a portion of at least one nucleic acid sequence of interest.

21. The composition can further include: a third primer configured to specifically hybridize to a first end of the at least one nucleic acid sequence of interest, and a fourth primer configured to specifically hybridize to a sequence complementary to a second end of the at least one nucleic acid sequence of interest.

22. A system that includes: a nucleic acid amplifier configured to amplify a nucleic acid sequence of interest in a sample comprising genomic DNA of a subject and amplify a reference sequence in the sample, a reagent reservoir containing at least a first primer configured to specifically hybridize to a first end of the at least one reference sequence, wherein the reference sequence has at least 80% sequence identity to at least one portion of genomic DNA comprising from about 60 to about 150 base pairs, wherein the at least one portion is present in chr1-121790-133586, chr1-329448-341534, chr1-648129-660266, chr1-222643865-228172047, chr1-243203764-243215874, chr10-38741930-38753964, chr11-114010-126106, chr16-90239446-90251554, chr19-183944-196032, chr2-114323560-114323652, chr2-243064480-243071940, chr20-62921559-62933673, chr3-197950387-197962431, chr4-119557144-120325498, chr4-165196360-165199636, chr5-180756063-180768074, chr6-170921836-170922549, chr7-39837560-63231088, chr7-128296352-128298474, chr8-143133-150475, chr9-49679-49771, chrY-26424506-27537936, or chr6-132951-145064; the at least one portion is present in at least a first minimum number of copies in the genome; and at least one copy of the at least one portion is present on each of at least a second minimum number of chromosomes; and a second primer configured to specifically hybridize to a sequence complementary to a second end of the at least one reference sequence; a detector configured to provide a first indication relating to an amount of the amplified sequence of interest and a second indication relating to an amount of the amplified reference sequence; and a controller configured to quantify the amplified sequence of interest relative to the amplified reference sequence, based at least in part on the first indication and the second indication; and determine a copy number of the sequence of interest from the relative quantified amplified sequence of interest.

23. In the system, the reference sequence can have at least 80% sequence identity to at least one of SEQ ID NO:1-31.

24. In the system, the reference sequence can have at least 80% sequence identity to at least one of SEQ ID NO:1-13.

25. In the system, the sample can include tissue suspected of being cancer tissue.

26. In the system, the sample has been subjected to formalin fixing and paraffin embedding (FFPE). 27. In the system, the controller is further configured to indicate the subject as having a cancer-related biomarker, based on the sequence of interest being associated with the cancer and the copy number being indicative of the cancer.

28. In the system, the nucleic acid amplifier is configured to amplify the sequence of interest and amplify the reference sequence by TaqMan quantitative polymerase chain reaction (qPCR).

29. A method that includes quantifying a nucleic acid sequence of interest in a sample comprising genomic DNA of a subject relative to a reference sequence in the sample, wherein the reference sequence has at least 80% sequence identity to at least one portion of genomic DNA comprising from about 60 to about 150 base pairs, wherein the at least one portion is present in chr1-121790-133586, chr1-329448-341534, chr1-648129-660266, chr1-222643865-228172047, chr1-243203764-243215874, chr10-38741930-38753964, chr11-114010-126106, chr16-90239446-90251554, chr19-183944-196032, chr2-114323560-114323652, chr2-243064480-243071940, chr20-62921559-62933673, chr3-197950387-197962431, chr4-119557144-120325498, chr4-165196360-165199636, chr5-180756063-180768074, chr6-170921836-170922549, chr7-39837560-63231088, chr7-128296352-128298474, chr8-143133-150475, chr9-49679-49771, chrY-26424506-27537936, or chr6-132951-145064; the at least one portion is present in at least a first minimum number of copies in the genome; and at least one copy of the at least one portion is present on each of at least a second minimum number of chromosomes; and determining a copy number of the sequence of interest from the relative quantified nucleic acid sequence of interest.

30. In the method, the reference sequence can have at least 80% sequence identity to at least one of SEQ ID NO:1-38.

31. In the method, the reference sequence can have at least 80% sequence identity to at least one of SEQ ID NO:1-13.

32. In the method, the sample includes tissue suspected of being cancer tissue.

33. In the method, the sample has been subjected to formalin fixing and paraffin embedding (FFPE) prior to amplifying the sequence of interest and amplifying the reference sequence.

34. The method can further include: diagnosing the subject as having a cancer-related biomarker, based on the sequence of interest being associated with the cancer and the copy number being indicative of the cancer.

The following examples are included to demonstrate particular embodiments of the disclosure. It should be appreciated by those of skill in the art that the techniques disclosed in the examples which follow represent techniques discovered by the inventor to function well in the practice of the disclosure, and thus can be considered to constitute particular modes for its practice. However, those of skill in the art should, in light of the present disclosure, appreciate that many changes can be made in the specific embodiments which are disclosed and still obtain a like or similar result without departing from the spirit and scope of the disclosure.

Example 1

SEQ ID NO:1-13 were identified by a two-stage process. First, a bioinformatics algorithm was used to identify candidate targets in the genome that met certain criteria associated with substantially normal copy number, even in cancer cells subjected to FFPE. Generally, sequences suspected of being relatively resistant to copy number abnormalities in cancer cells and/or cells subjected to FFPE were used to query publicly-available human genomic databases, and only those sequences returning multiple hits were considered as candidate targets for further testing.

The first stage identified SEQ ID NO:1-31. SEQ ID NO:2-8 and 10-13 are located in the genome at the loci given supra. SEQ ID NO:14-31 are located in the genome at least at the following loci:

SEQ ID NO:14, chr10 38753941 . . . 38753964 . . . 38754039 chr11.11250s.

SEQ ID NO:15, chr10 38753848 . . . 38753866 . . . 38753912 chr11.11350s.

SEQ ID NO:16, chr10 38753856 . . . 38753896 . . . 38753934 chr1.5850s.

SEQ ID NO:17, chr10 38753715 . . . 38753794 . . . 38753862 chr1.5950s.

SEQ ID NO:18, chr10 38753145 . . . 38753206 . . . 38753248 chr16.2650s.

SEQ ID NO:19, chr10 38753377 . . . 38753408 . . . 38753457 chr16.2850s.

SEQ ID NO:20, chr10 38753232 . . . 38753257 . . . 38753351 chr20.2650s.

SEQ ID NO:21, chr10 38753326 . . . 38753360 . . . 38753411 chr20.2750s.

SEQ ID NO:22, chr10 38753413 . . . 38753454 . . . 38753513 chr20.2850s.

SEQ ID NO:23, chr11 123673 . . . 123696 . . . 123739 chr20.3850s.

SEQ ID NO:24, chr10 38750797 . . . 38750847 . . . 38750889 chr3.150s.

SEQ ID NO:25, chr10 38741930 . . . 38741975 . . . 38742018 chr3.1550s.

SEQ ID NO:26, chr10 38742246 . . . 38742274 . . . 38742312 chr3.1850s.

SEQ ID NO:27, chr10 38746651 . . . 38746676 . . . 38746733 chr3.6250s.

SEQ ID NO:28, chr10 38753090 . . . 38753126 . . . 38753234 chr5.2550s.

SEQ ID NO:29, chr10 38753486 . . . 38753535 . . . 38753587 chr5.2950s.

SEQ ID NO:30, chr10 38753797 . . . 38753835 . . . 38753885 chr5.3250s.

SEQ ID NO:31, chr10 38753907 . . . 38753935 . . . 38753971 chr5.3350s.

| Twenty-three larger regions to which the candidate sequences mapped were as follows: Region | Chromosome | Starting position | Ending position |
|---|---|---|---|
| 1 | chr1 | 121790 | 133586 |
| 2 | chr1 | 329448 | 341534 |
| 3 | chr1 | 648129 | 660266 |
| 4 | chr1 | 222643865 | 228172047 |
| 5 | chr1 | 243203764 | 243215874 |
| 6 | chr10 | 38741930 | 38753964 |
| 7 | chr11 | 114010 | 126106 |
| 8 | chr16 | 90239446 | 90251554 |
| 9 | chr19 | 183944 | 196032 |
| 10 | chr2 | 114323560 | 114323652 |
| 11 | chr2 | 243064480 | 243071940 |
| 12 | chr20 | 62921559 | 62933673 |
| 13 | chr3 | 197950387 | 197962431 |
| 14 | chr4 | 119557144 | 120325498 |
| 15 | chr4 | 165196360 | 165199636 |
| 16 | chr5 | 180756063 | 180768074 |
| 17 | chr6 | 170921836 | 170922549 |
| 18 | chr7 | 39837560 | 63231088 |
| 19 | chr7 | 128296352 | 128298474 |
| 20 | chr8 | 143133 | 150475 |
| 21 | chr9 | 49679 | 49771 |

| Twenty-three larger regions to which the candidate sequences mapped were as follows: Region | Chromosome | Starting position | Ending position |
|---|---|---|---|
| 22 | chrY | 26424506 | 27537936 |
| 23 | chr6 | 132951 | 145064 |

(As the person of ordinary skill in the art is aware, as of this writing, the resistance of a sequence to copy number abnormalities in cancer cells and/or cells subjected to FFPE cannot be predicted with sufficient accuracy from sequence data alone. Further testing, such as that described below, is required to identify sequences suitable for use as a multicopy reference assay).

Numerous qPCR, TaqMan reference assays were designed using the candidate targets and tested on cancer samples alongside a qPCR, TaqMan target of interest (TOI) assay. The assays mapped to the target regions many-fold:

| id | number of hits | number of chromosomes |
|---|---|---|
| chr11.11250s.1 | 16 | 11 |
| chr11.11350s.1 | 17 | 12 |
| chr1.5850s.1 | 17 | 11 |
| chr1.5950s.1 | 15 | 11 |
| chr16.2650s.1 | 15 | 11 |
| chr16.2850s.1 | 15 | 11 |
| chr16.3250s.1 | 16 | 11 |
| chr16.3350s.1 | 16 | 11 |
| chr20.2650s.1 | 16 | 11 |
| chr20.2750s.1 | 16 | 11 |
| chr20.2850s.1 | 16 | 11 |
| chr20.3250s.1 | 17 | 12 |
| chr20.3350s.1 | 16 | 11 |
| chr20.3850s.1 | 17 | 11 |
| chr2.3250s.1 | 15 | 11 |
| chr3.150s.1 | 15 | 12 |
| chr3.1550s.1 | 16 | 11 |
| chr3.1850s.1 | 23 | 11 |
| chr3.6250s.1 | 18 | 13 |
| chr5.2550s.1 | 17 | 12 |
| chr5.2850s.1 | 15 | 11 |
| chr5.2950s.1 | 19 | 13 |
| chr5.3250s.1 | 17 | 12 |
| chr5.3350s.1 | 16 | 11 |

After initial testing, two targets provided results suggestive of substantially normal copy number, even in cancer cells subjected to FFPE, and were selected for a final round of testing on an expanded panel of samples.

The final round of testing evaluated the performance of these two de novo qPCR multicopy reference assays, a conventional qPCR single copy reference assay (RNaseP) and five qPCR TOI assays for the IRS2 gene. The qPCR assays all used as template genomic DNA extracted from 35 colorectal normal tissue samples subjected to FFPE. All assays were performed in duplicate, with the reference assay and target of interest assay run in separate wells to generate accurate Cq values.

The first multicopy reference assay, corresponding to SEQ ID NO:1-8, used a first set comprising forward primer, reverse primer, and probe sequence. The second multicopy reference assay, corresponding to SEQ ID NO:9-13, used a second set comprising forward primer, reverse primer, and probe sequence.

Figure 3B:
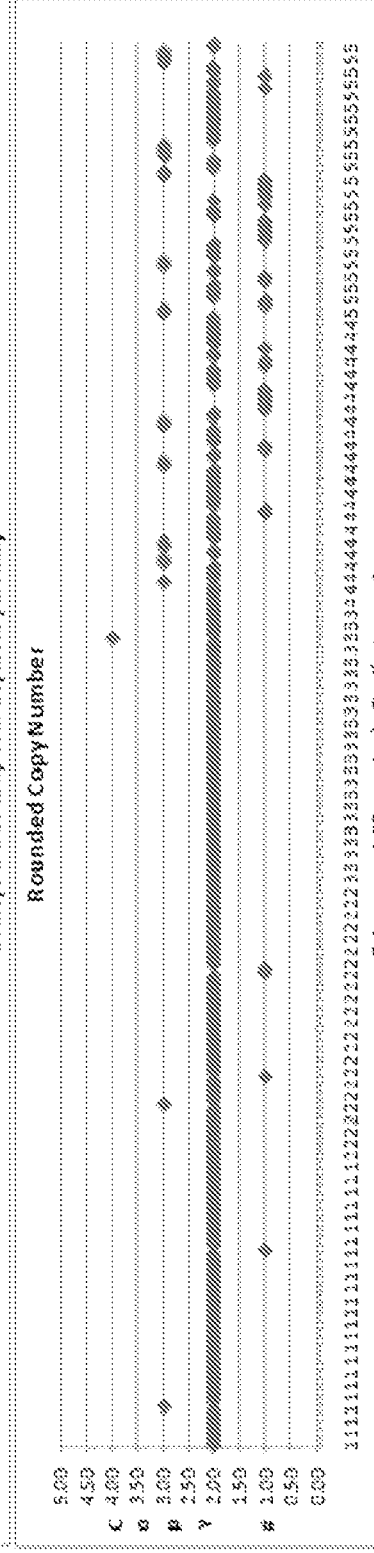
FIG. 3B shows the rounded copy number of IRS2 as determined by qPCR with a reference assay based on SEQ ID NO:9-13.

The expectation was that a result of 2 copies for the IRS2 gene should be determined for normal samples, if a test generated accurate results. A snapshot summary of the results is provided in FIGS. 1A-3B for each of the three reference assays: RNaseP (FIGS. 1A-1B), SEQ ID NO:1-8 (FIGS. 2A-2B), and SEQ ID NO:9-13 (FIGS. 3A-3B). In each figure, the copy number is plotted on the y-axis and the 35 samples in duplicate times the five different IRS2 TOI assays are plotted on the x-axis. Each figure contains 350 data points.

The results depended not only on the reference assay used, but also the IRS2 TOI assay used. The two multicopy reference assays performed well, along with the first 3 IRS2 TOI assays. In each figure, subfigure A has decimal point calculated copy number, and subfigure B has rounded copy number.

All of the compositions, methods, and/or systems disclosed and claimed herein can be made and executed without undue experimentation in light of the present disclosure. While the compositions and methods of this disclosure have been described in terms of particular embodiments, it will be apparent to those of skill in the art that variations may be applied to the compositions, methods, and/or systems and in the steps or in the sequence of steps of the method described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

What is claimed is:

1. A method, comprising:
  amplifying a nucleic acid sequence of interest in a sample comprising genomic DNA of a human subject;
  amplifying a reference sequence in the sample, wherein the reference sequence comprises SEQ ID NO: 1, 6 or 7,
    wherein at least one copy of the reference sequence is present on at least ten chromosomes of the genomic DNA of the human subject,
    wherein said amplifying the nucleic acid sequence of interest and said amplifying the reference sequence are both performed by TaqMan quantitative polymerase chain reaction (qPCR),
    and wherein said sample has been subjected to formalin fixing and paraffin embedding (FFPE) prior to said amplifying the nucleic acid sequence of interest and said amplifying the reference sequence;
  quantifying the amplified sequence of interest relative to the amplified reference sequence using two probes, each comprising a fluorescent moiety at a first end and a quencher for that fluorescent moiety at a second end, with one probe specifically hybridizing to the sequence of interest and the other specifically hybridizing to the reference sequence; and
  determining a copy number of the sequence of interest from the relative quantified amplified sequence of interest.

2. The method of claim 1, wherein the sample comprises tissue suspected of being cancer tissue.

3. The method of claim 2, further comprising:
  diagnosing the human subject as having a cancer-related biomarker, based on the sequence of interest being associated with the cancer and the copy number being indicative of the cancer.

4. The method of claim 1, further comprising:
  diagnosing the human subject as having a cancer-related biomarker, based on the sequence of interest being associated with the cancer and the copy number being indicative of the cancer.

5. The method of claim 1, wherein the reference sequence further comprise any of SEQ ID NO: 9-31 or a sequence that has at least 90% sequence identity to at least one of SEQ ID NO: 9-31.

6. The method of claim 1, wherein the reference sequence further comprise any of SEQ ID NO: 9-13 or a sequence that has at least 90% sequence identity to at least one of SEQ ID NO: 9-13.

* * * * *